US006471967B1

(12) United States Patent
Horwitz et al.

(10) Patent No.: US 6,471,967 B1
(45) Date of Patent: Oct. 29, 2002

(54) RECOMBINANT INTRACELLULAR PATHOGEN VACCINES AND METHODS FOR USE

(75) Inventors: Marcus A. Horwitz; Gunter Harth, both of Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/550,468

(22) Filed: Apr. 17, 2000

(51) Int. Cl.[7] .................. A61K 39/04; A61K 39/02; A61K 39/00; A61K 39/38; C12N 15/00

(52) U.S. Cl. .................. 424/248.1; 424/9.1; 424/9.2; 424/184.1; 424/185.1; 424/192.1; 424/200.1; 424/234.1; 435/320.1

(58) Field of Search .................. 424/9.1, 9.2, 184.1, 424/185.1, 192.1, 200.1, 234.1, 248.1; 435/320.1

(56) References Cited

U.S. PATENT DOCUMENTS

| | | |
|---|---|---|
| 5,504,005 A | 4/1996 | Bloom et al. |
| 5,583,038 A | 12/1996 | Stover |
| 5,591,632 A | 1/1997 | O'Donnell et al. |
| 5,679,515 A | 10/1997 | Stover et al. |
| 5,700,683 A | 12/1997 | Stover et al. |
| 5,736,367 A | 4/1998 | Haun et al. |
| 5,776,465 A | 7/1998 | O'Donnell et al. |
| 5,807,723 A | 9/1998 | Aldovini et al. |
| 5,830,475 A | 11/1998 | Aldovini et al. |
| 5,854,055 A | 12/1998 | Bloom et al. |
| 5,866,403 A | 2/1999 | Aldovini et al. |
| 5,869,057 A | 2/1999 | Rock |
| 6,015,696 A | 1/2000 | Yamada et al. |

FOREIGN PATENT DOCUMENTS

WO    WO 88/06626 A1    9/1988

OTHER PUBLICATIONS

Lee et al., T–Cell Epitope Mapping of the Three Most Abundant Extracellular Proteins of Mycobacterium tuberculosis in Outbred Guinea Pigs, Infection and Immunity, May 1999, p. 2665–2670, vol. 67, No. 5.
Horwitz et al., Recombinant bacillus Calmette–Guérin (BCG) vaccines expressing the Mycobacterium tuberculosis 30–kDa major secretory protein induce greater protective immunity against tuberculosis than conventional BCG vaccines in a highly susceptible animal model, PNAS, Dec. 5, 2000, vol. 97, No. 25.
Ohara et al.. Inhibition of Multiplication of Mycobacterium Laprae in Mouse Foot Pads by Recombinant Bacillus Catmette–Guérin (BCG); Vaccine 19 (2000) 1294–1297.
Naito et al, The Antigen 85 Complex Vaccine Against Experimental Mycobacterium Leprae Infection in Mice; Vaccine 18 (2000), 795–798.
Ohara, et al.; Characterization of the Transcriptional Initiation Regions of Genes for the Major Secreted Protein Antigens 85C and MPB51 of Mycobacterium Bovis BCG.
Bacterial Vaccine Vectors and Bacillus Calmette–Guerin, Jeffrey D. Cirillo, et al., Clinical Infectious Diseases, 1995; 20: 1001–9.
New Use of BCG for Recombinant Vaccines, C.K. Stover, et al., Nature, vol. 351, Jun. 6, 1991.
Systemic and Mucosal Immunity Induced by BCG Vector Expressing Outer–Surface Protein A of Borrelia Burgdorferi, Solomon Langermann, et al., Nature, vol. 372, Dec. 8, 1994.
Protective Humoral Response Against Pneumococcal Infection in Mice Elicited by Recombinant Bacille Calmette–Guerin Vaccines Expressing Pneumococcal Surface Protein A, Solomon Langermann, et al., J. Exp. Med., The Rockefeller University Press, vol. 180, Dec. 1994, 2277–2286.
Protective Immunity Elicited by Recombinant Bacille Calmette–Guerin (BCG) Expressing Outer Surface Protein A (OspA) Lipoprotein: A Candidate Lyme Disease Vaccine, C. Kendall Stover, et al., J. Exp. Med., The Rockefeller University Press, vol. 178, Jul. 1993, 197–209.
Immunization with Recombinant BCG–SIV Elicits SIV–Specific Cytotoxic T Lymphocytes in Rhesus Monkeys, Yasuhiro Yasutomi, et al., The Journal of Immunology, vol. 150, 3101–3107, No. 7, Apr. 1, 1993.
Development and Analysis of Recombinant BCG Vector Systems, Thomas R. Fuerst, et al., AIDS Research and Human Retroviruses, vol. 8, No. 8, 1992.
Use of Recombinant BCG as a Vaccine Delivery Vehicle, C. Kendall Stover, et al., Advances in Experimental Medicine and Biology, vol. 327.

(List continued on next page.)

*Primary Examiner*—Rodney P Swartz
(74) *Attorney, Agent, or Firm*—Oppenheimer Wolff & Donnelly LLP; Louis C. Cullman (57) ABSTRACT

Vaccines and immunotherapeutics for preventing intracellular pathogen diseases in mammals are provided that consist of recombinant attenuated intracellular pathogens that have been transformed to express recombinant immunogenic antigens of the same or other intracellular pathogens. Exemplary vaccines and immunotherapeutics include attenuated recombinant Mycobacteria expressing the major extracellular non-fusion proteins of Mycobacteria and/or other intracellular pathogens. These exemplary vaccines are shown to produce surprisingly potent protective immune responses in mammals that surpass those of any previously known anti-mycobacterium vaccine. More specifically, a recombinant BCG expressing the 30 kDa major extracellular non-fusion protein of *Mycobacterium tuberculosis* is provided. Additionally, methods for preventing and treating diseases caused by intracellular pathogens are provided. The methods of treating and preventing intracellular pathogen diseases utilize the described surprisingly efficacious vaccines and immunotherapeutics.

6 Claims, 5 Drawing Sheets

OTHER PUBLICATIONS

Protective Immunity Elicited by rBCG Vaccines, C. K. Stover, et al., Brown F(ed) Recombinant Vectors in Vaccine Development, Dev Biol Stand. Basel, Karger, 1994, vol. 82, pp 163–170.

Efficacy and Safety of Live Recombinant BCG Vaccines, M. S. Hanson, et al., Non–Target Effects of Live Vaccines, Dev Biol Stand. Basel, Karger, 1995, vol. 84, pp 229–236.

High–Level Heterologous Expression and Secretion in Rapidly Growing Nonpathogenic Mycobacteria of Four Major Mycobacterium Tuberculosis Extracellular Proteins Considered to be Leading Vaccine Candidates and Drug Targets, Gunter Harth, et al., Infection and Immunity, Jun. 1997, p. 2321–2328.

Novel Insights into the Genetics, Biochemistry, and Immunocytochemistry of the 30–Kilodalton Major Extracelluar Protein of Mycobacterium Tuberculosis, Gunter Harth, et al., Infection and Immunity, Aug. 1996, p. 3038–3047.

Experiment 2: Weights of Guinea Pigs After Challenge

RECOMBINANT INTRACELLULAR PATHOGEN VACCINES AND METHODS FOR USE

REFERENCE TO GOVERNMENT

This invention was made with Government support under Grant No. AI31338 awarded by the Department of Health and Human Services. The Government has certain rights in this invention.

FIELD OF THE INVENTION

The present invention generally relates to immunotherapeutic agents an d vaccines against intracellular pathogenic organisms such as bacteria, protozoa, viruses and fingi. More specifically, unlike prior art vaccines and immunotherapeutic agents based upon pathogenic subunits, killed pathogens and attenuated natural pathogens, the present invention uses recombinant attenuated pathogens, or closely related species, that express and secrete immunogenic determinants of a selected pathogen stimulating an effective immune response in mammalian hosts. The immunostimulatory vaccines and immunotherapeutics of the present invention are derived from recombinant attenuated intracellular pathogens, or closely related species, that express immunogenic determinants in situ.

BACKGROUND OF THE INVENTION

It has long been recognized that parasitic microorganisms possess the ability to infect animals thereby causing disease and often the death of the host. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms is evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus mycobacterium and the genus Legionella, complete all or part of their lifecycle within the cells of the infected host organism rather than extracellularly. Around the world, intracellular bacteria are responsible for millions of deaths each year and untold suffering. Tuberculosis is the leading cause of death from a single disease agent worldwide, with 10 million new cases and 2.9 million deaths every year. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, and legionellosis. At this time, relatively little can be done to prevent debilitating infections in susceptible individuals exposed to many of these organisms Due to this inability to effectively protect populations from such intracellular pathogens and the resulting human and animal morbidity and mortality caused by such agents, tuberculosis, is one of the most important diseases now confronting mankind.

Those skilled in the art will appreciate that the following exemplary discussion of *M. tuberculosis* is illustrative of the teachings of the present invention and is in no way intended to limit the scope of the present invention to the treatment of *M. tuberculosis*. Similarly, the teachings herein are not limited in any way to the treatment of tubercular infections. On the contrary, this invention may be used to advantageously provide safe and effective vaccines and immunotherapeutic agents against any pathogenic agent by using recombinant attenuated pathogens, or recombinant avirulent organisms, to express, and of equal importance to release the immunologically important proteins of the pathogenic organism.

Currently it is believed that approximately one-third of the world's population is infected by *M. tuberculosis* resulting in millions of cases of pulmonary tuberculosis annually. More specifically, human pulmonary tuberculosis primarily caused by *M. tuberculosis* is a major cause of death in developing countries. Capable of surviving inside macrophages and monocytes, *M. tuberculosis* may produce a chronic intracellular infection. *M. tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore prevented the development of fully effective immunotherapeutic agents or vaccines against tubercular infections.

While this disease is a particularly acute health problem in the developing countries of Latin America, Africa, and Asia, it is also becoming more prevalent in the first world. In the United States specific populations are at increased risk, especially urban poor, immunocompromised individuals and immigrants from areas of high disease prevalence. Largely due to the AIDS epidemic, in recent years the incidence of tuberculosis has increased in developed countries, often in the form of multi-drug resistant *M. tuberculosis*.

Recently, tuberculosis resistance to one or more drugs was reported in 36 of the 50 United States. In New York City, one-third of all cases tested was resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, safe and effective vaccines against such varieties of *M. tuberculosis* are sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus Mycobacterium also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic vector of the genus Mycobacterium is *M. leprae* that causes millions of cases of the ancient disease leprosy. Other species of this genus which cause disease in animals and man include *M. kansasii, M. aviuim intracellulare, M. fortuitum, M. marinum, M. chelonei*, and *M. scrofulaceum*. The pathogenic mycobacterial species frequently exhibit a high degree of homology in their respective DNA and corresponding protein sequences and some species, such as *M. tuberculosis* and *M. bovis,* are highly related.

For obvious practical and moral reasons, initial work in humans to determine the efficacy of experimental compositions with regard to such afflictions is infeasible. Accordingly, in the early development of any drug or vaccine it is standard procedure to employ appropriate animal models for reasons of safety and expense. The success of implementing laboratory animal models is predicated on the understanding that immunogenic epitopes are frequently active in different host species. Thus, an immunogenic determinant in one species, for example a rodent or guinea pig, will generally be immunoreactive in a different species such as in humans. Only after the appropriate animal models are sufficiently developed will clinical trials in humans be carried out to further demonstrate the safety and efficacy of a vaccine in man.

With regard to alveolar or pulmonary infections by *M. tuberculosis,* the guinea pig model closely resembles the human pathology of the disease in many respects. Accordingly, it is well understood by those skilled in the art that it is appropriate to extrapolate the guinea pig model of this disease to humans and other mammals. As with humans, guinea pigs are susceptible to tubercular infection with low doses of the aerosolized human pathogen *M. tuberculosis*. Unlike humans where the initial infection is usually controlled, guinea pigs consistently develop disseminated disease upon exposure to the aerosolized pathogen, facilitating subsequent analysis. Further, both guinea pigs and humans display cutaneous delayed-type hypersensitivity reactions characterized by the development of a dense mononuclear cell induration or rigid area at the skin test site. Finally, the characteristic tubercular lesions of humans and guinea pigs exhibit similar morphology including the presence of Langhans giant cells. As guinea pigs are more susceptible to initial infection and progression of the disease than humans, any protection conferred in experiments using this animal model provides a strong indication that the same protective immunity may be generated in man or other less susceptible mammals. Accordingly, for purposes of explanation only and not for purposes of limitation, the present invention will be primarily demonstrated in the exemplary context of guinea pigs as the mammalian host. Those skilled in the art will appreciate that the present invention may be practiced with other mammalian hosts including humans and domesticated animals.

Any animal or human infected with a pathogenic organism and, in particular, an intracellular organism, presents a difficult challenge to the host immune system. While many infectious agents may be effectively controlled by the humoral response and corresponding production of protective antibodies, these mechanisms are primarily effective only against those pathogens located in the body's extracellular fluid. In particular, opsonizing antibodies bind to extracellular foreign agents thereby rendering them susceptible to phagocytosis and subsequent intracellular killing. Yet this is not the case for other pathogens. For example, previous studies have indicated that the humoral immune response does not appear to play a significant protective role against infections by intracellular bacteria such as *M. tuberculosis*. However, the present invention may generate a beneficial humoral response to the target pathogen and, as such, its effectiveness is not limited to any specific component of the stimulated immune response.

More specifically, antibody mediated defenses seemingly do not prevent the initial infection of intracellular pathogens and are ineffectual once the bacteria are sequestered within the cells of the host. As water soluble proteins, antibodies can permeate the extracellular fluid and blood, but have difficulty migrating across the lipid membranes of cells. Further, the production of opsonizing antibodies against bacterial surface structures may actually assist intracellular pathogens in entering the host cell. Accordingly, any effective prophylactic measure against intracellular agents, such as Mycobacterium, should incorporate an aggressive cell-mediated immune response component leading to the rapid proliferation of antigen specific lymphocytes that activate the compromised phagocytes or cytotoxically eliminate them. However, as will be discussed in detail below, inducing a cell-mediated immune response does not equal the induction of protective immunity. Though cell-mediated immunity may be a prerequisite to protective immunity, the production of vaccines in accordance with the teachings of the present invention requires animal based challenge studies.

This cell-mediated immune response generally involves two steps. The initial step, signaling that the cell is infected, is accomplished by special molecules (major histocompatibility or MHC molecules) which deliver pieces of the pathogen to the surface of the cell. These MHC molecules bind to small fragments of bacterial proteins that have been degraded within the infected cell and present them at the surface of the cell. Their presentation to T-cells stimulates the immune system of the host to eliminate the infected host cell or induces the host cell to eradicate any bacteria residing within.

Attempts to eradicate tuberculosis using vaccination was initiated in 1921 after Calmette and Guérin successfully attenuated a virulent strain of *M. bovis* using in vitro serial passage techniques. The resultant live vaccine developed at the Institut Pasteur in Lille, France is known as the Bacille Calmette and Guérin, or BCG vaccine. Nearly eighty years later this vaccine remains the only prophylactic therapy for tuberculosis currently in use. In fact all BCG vaccines available today are derived from the original strain of *M. bovis* developed by Calmette and Guérin at the Institut Pasteur.

The World Health Organization considers the BCG vaccine an essential factor in reducing tuberculosis worldwide, especially in developing nations. In theory, BCG vaccine confers cell-mediated immunity against an attenuated mycobacterium that is immunologically related to *M. tuberculosis*. The resulting immune response should prevent primary tuberculosis. Thus, if primary tuberculosis is prevented, latent infections cannot occur and disease reactivation is avoided.

However, controlled clinical trials have revealed significant variations in vaccine efficacy. Reported efficacy rates have varied between 0–80%. Vaccine trials conducted in English school children reported a ten-year post vaccination protection rate in excess of 78%. However, in a similar trial in South India, BCG failed to protect against culture-proven primary tuberculosis in the first 5 years post inoculation. A recent meta-analysis of BCG efficacy in the prevention of tuberculosis estimated that overall prophylactic efficacy was approximately 50%. (Colditz, G. A. T. F. Brewer, C. S. Berkey, M. E. Wilson, E. Burdick, H. V. Fineberg, and F. Mosteller. 1994. JAMA 271:698–702.)

This remarkable disparity in reported efficacy rates remains a vexing problem for health officials and practitioners that must determine when and how to use the BCG vaccine. Numerous factors have been implicated that may account for these observed efficacy disparities including differences in manufacturing techniques, routes of inoculation and characteristics of the populations and environments in which the vaccines have been used. Recent work suggests that incidental contact with environmental mycobacteria may result in a "natural vaccine" that prevents the vaccine recipient from mounting an effective response to native BCG proteins.

In order to minimize BCG immunogenicity variation, vaccine manufactures maintain master stocks of original vaccine strains in the lyophilized (freeze dried) state. Each production strain derived therefrom is in turn named after the manufacturing site, company or bacterial strain, for example: BCG-London, BCG-Copenhagen, BCG-Connaught, or BCG-Tice (marketed worldwide by Organon, Inc.). In an effort to standardize manufacturing techniques in the United States, the Federal Food and Drug Administration's (FDA) Center for Biologic Education and Research (CBER) regulates vaccine manufacturing. The FDA's CBER branch has specified that each lyophilized BCG strain used for vaccination must be capable of inducing a specified tuberculin skin test reaction in guinea pigs and humans. Unfortunately, induced tuberculin sensitivity has not been shown to correlate with protective immunity.

Current BCG vaccines are provided as lyphophilzed cultures that are re-hydrated with sterile diluent immediately before administration. The BCG vaccine is given at birth, in infancy, or in early childhood in countries that practice BCG vaccination, including developing and developed countries. Adult visitors to endemic regions who may have been exposed to high doses of infectious mycobacteria may receive BCG as a prophylactic providing they are skin test non-reactive. Adverse reactions to the vaccine are rare and are generally limited to skin ulcerations and lymphadenitis near the injection site. However, in spite of these rare adverse reactions, the BCG vaccine has an unparalleled history of safety with over three billion doses having been administered worldwide since 1930.

Eighty-years have now passed since BCG was developed and there remains paucity in acceptable vaccine alternatives. Recently, the present inventors have made considerable progress in the isolation, characterization and recombinant expression of extracellular proteins secreted by intracellular pathogens. For example, the inventors' U.S. Pat. No. 5,108,745, issued Apr. 28, 1992 and several pending U.S. Patent applications provide vaccines and methods of producing protective immunity against *L. pneumophila* and *M. tuberculosis* as well as other intracellular pathogens. These prior art vaccines are broadly based on extracellular products originally derived from proteinaceous compounds released extracellularly by the pathogenic bacteria into broth culture in vitro and released extracellularly by bacteria within infected host cells in vivo. As provided therein, these vaccines are selectively based on the identification of extracellular products or their analogs that stimulate a strong immune response against the target pathogen in a mammalian host Vaccines prepared from selected *M. tuberculosis* extracellular products are currently being optimized for use as human prophylactic therapies. Protein cocktails and individual protein preparations using both recombinant as well as naturally expressed proteins are being studied. One goal of these ongoing studies is to maximize the base immune response through optimum immunogen (protein) presentation. To date over 100 different preparations have been made including 38 different protein combinations, 26 different adjuvants, 10 different protein concentrations and seven different dosing regimens. The candidate vaccine proteins have also been coupled to non-*M. tuberculosis* proteins including bovine serum albumin, Legionella sp. major secretory protein, and tetanus toxoid. This list is not inclusive of methods the present inventors have used to present extracellular proteins of intracellular pathogens to host animals; rather it illustrates the enormous complexity and inherent variability associated with vaccine optimization. However, in spite of these and other activities, no combination of extracellular proteins, adjuvants, carrier proteins, concentrations or dosing frequencies resulted in inducing a protective immune response in guinea pigs that was comparable or superior to BCG.

Recently, significant attention has been focused on using transformed BCG strains to produce vaccines that express various cell-associated antigens. For example, C. K. Stover, et al. have reported a Lyme Disease vaccine using a recombinant BCG (rBCG) that expresses the membrane associated lipoprotein OspA of *Borrelia burgdorferi*. Similarly, the same author has also produced a rBCG vaccine expressing a pneumococcal surface protein (PsPA) of *Streptococcus pneumoniae*. (Stover, C. K., G. P. Bansal, S. Langerman, and M. S. Hanson. 1994. *Protective Immunity Elicited by rBCG Vaccines*. In: Brown F. (ed): Recombinant Vectors in Vaccine Development. Dev Biol Stand. Dasel, Karger, Vol. 82, 163–170.)

U.S. Pat. No. 5,504,005 (the "'005" patent") and U.S. Pat. No. 5,854,055 (the "'055 patent") both issued to B. R. Bloom et al., disclose theoretical rBCG vectors expressing a wide range of cell associated fusion proteins from numerous species of microorganisms. The theoretical vectors described in these patents are either directed to cell associated fusion proteins, as opposed to extracellular non-fusion protein antigens, and/or the rBCG is hypothetically expressing fusion proteins from distantly related species. Moreover, the recombinant cell associated fusion proteins expressed in these models are encoded on DNA that is integrated into the host genome and under the control of heat shock promoters.

Consequently, the antigens expressed are fusion proteins and expression is limited to levels approximately equal to, or less than, the vector's native proteins.

Furthermore, neither the '005 nor the '055 patent disclose animal model safety testing, immune response development or protective immunity in an animal system that closely emulates human disease. In addition, only theoretical rBCG vectors expressing *M. tuberculosis* fusion proteins are disclosed in the '005 and '055, no actual vaccines are enabled. Those vaccine models for *M. tuberculosis* that are disclosed are directed to cell associated heat shock fusion proteins, not extracellular non-fusion proteins.

U.S. Pat. No. 5,830,475 (the "'475 patent") also discloses theoretical mycobacterial vaccines used to express fusion proteins. The DNA encoding for these fusion proteins resides in extrachromasomal plasmids under the control of mycobacterial heat shock protein and stress protein promoters. The vaccines disclosed are intended to elicit immune responses in non-human animals for the purpose of producing antibodies thereto and not shown to prevent intracellular pathogen diseases in mammals. Moreover, the '475 patent does not disclose recombinant vaccinating agents that use protein specific promoters to express extracellular non-fusion proteins.

The present inventors propose, without limitation, that major extracellular non-fusion proteins of intracellular pathogens may be important immunoprotective molecules. First extracellular non-fusion proteins, by virtue of their release by the pathogen into the intracellular milieu of the host cell, are available for processing and presentation to the immune system as fragments bound to MHC molecules on the host cell surface. These peptide-MHC complexes serve to alert the immune system to the presence within the host cell of an otherwise hidden invader, enabling the immune system to mount an appropriate anti-microbial attack against the invader. Second, effective immunization with extracellular proteins is able to induce a population of immune cells that recognize the same peptide-MHC complexes at some future time when the complexes are displayed on host cells invaded by the relevant intracellular pathogen. The immune cells are thus able to target the infected host cells and either activate them with cytokines, thereby enabling them to restrict growth of the intracellular pathogen, or lyse them, thereby denying the pathogen the intracellular milieu in which it thrives. Third, among the extracellular proteins, the major ones, i.e., those produced most abundantly, will figure most prominently as immunoprotective molecules since they would generally provide the richest display of peptide-MHC complexes to the immune system Therefore, there remains a need for recombinant intracellular pathogen vaccines that express major extracellular non-fusion proteins of intracellular pathogens that are closely related to the vaccinating agent. Furthermore, there is a need for recombinant intracellular pathogen vaccines that are capable of over-expressing recombinant extracellular non-fusion proteins by virtue of extrachromosomal DNA having non-heat shock gene promoters or non-stress protein gene promoters.

Specifically, there remains an urgent need to produce intracellular pathogen vaccines that provide recipients protection from diseases that is superior to the protection afforded BCG vaccine recipients. Moreover, there is an urgent need to provide both developed and developing countries with a cost efficient, immunotherapeutic and prophylactic treatment for tuberculosis and other intracellular pathogens.

Therefore, it is an object of the present invention to provide therapeutic and prophylactic vaccines for the treatment and prevention of disease caused by intracellular pathogens.

It is another object of the present invention to provide vaccines for preventing intracellular pathogen diseases using intracellular pathogens that have been transformed to express the major recombinant immunogenic antigens of the same intracellular pathogen, another intracellular pathogen, or both.

It is yet another object of the present invention to provide vaccines for the treatment and prevention of mycobacteria diseases using recombinant BCG that expresses the extracellular protein(s) of a pathogenic mycobacterium.

It is another object of the present invention to provide vaccines for treatment and/or prevention of tuberculosis using recombinant strains of BCG that express and secrete one or more major extracellular proteins of *Mycobacterium tuberculosis.*

SUMMARY OF THE INVENTION

The present invention accomplishes the above-described and other objects by providing a new class of vaccines and immunotherapeutics and methods for treating and preventing intracellular pathogen diseases in mammals. Historically intracellular pathogen vaccines and immunotherapeutics have been prepared from the intracellular pathogen itself or a closely related species. These old vaccine models were composed of the entire microorganism or subunits thereof. For example, the first, and currently only available vaccine, for *Mycobacterium tuberculosis* is an attenuated live vaccine made from the closely related intracellular pathogen *M. bovis.* Recently, the present inventors have discovered that specific extracellular products of intracellular pathogens that are secreted into growth media can be used to illicit protective immune responses in mammals either as individual subunits, or in subunit combinations. However, these subunit vaccines have not proven to be superior to the original attenuated vaccine derived from *M. bovis.*

The present invention details vaccines and immunotherapeutics composed of recombinant attenuated intracellular pathogens (vaccinating agents) that have been transformed to express the extracellular protein(s) (recombinant immunogenic antigens) of another or same intracellular pathogen. In one embodiment the vaccines of the present invention are made using recombinant strains of the Bacille Calmette and Guérin, or BCG. In this embodiment the recombinant BCG expresses major extracellular proteins of pathogenic mycobacteria including, but not limited to, *M. tuberculosis, M. leprae* and *M. bovis,* to name but a few.

The major extracellular proteins expressed by the recombinant BCG include, but are not limited to, the 12 kDa, 14 kDa, 16 kDa, 23 kDa, 23.5 kDa, 30 kDa, 32A kDa, 32B kDa, 45 kDa, 58 kDa, 71 kDa, 80 kDa, and 110 kDa of Mycobacterium sp. and respective analogs, homologs and subunits thereof including recombinant non-fusion proteins, fusion proteins and derivatives thereof. It is apparent to those of ordinary skill in the at that the molecular weights used to identify the major extracellular proteins of Mycobacteria and other intracellular pathogens are only intended to be approximations. Those skilled in the art of recombinant technology and molecular biology will realize that it is possible to co-express (co-translate) these proteins with additional amino acids, polypeptides and proteins, as it its also possible to express these proteins in truncated forms. The resulting modified proteins are still considered to be within the scope of the present invention whether termed native, non-fusion proteins, fusion proteins, hybrid proteins or chimeric proteins. For the purposes of the present invention, fusion proteins are defined to include, but not limited to, the products of two or more coding sequences from different genes that have been cloned together and that, after translation, form a single polypeptide sequence.

The present invention also describes recombinant attenuated intracellular pathogen vaccinating agents that over express non-fusion proteins from at least one other intracellular pathogen. This is accomplished by using extrachromosomal nucleic acids to express at least one recombinant immunogenic antigen gene and placing this gene(s) under the control of non-heat shock gene promoters or non-stess protein gene promoters, preferably protein-specific promoter sequences. Consequently, vaccines are provided having non-fusion, recombinant immunogenic antigens expressed in greater quantities than possible when genes encoding for recombinant immunogenic antigens are stably integrated into the vaccinating agent's genomic DNA. As a result, intracellular pathogen vaccines having surprisingly superior specificity and potency than existing subunit or attenuated intracellular pathogen vaccines are provided.

Moreover the present invention describes methods of treating and preventing mammalian diseases caused by intracellular pathogens using the vaccines of the present invention. A partial list of the many intracellular pathogens that may be used as the attenuated vaccinating agents and/or the source of the recombinant immunogenic antigens includes, but is not limited to, *Mycobacterium bovis, M. tuberculosis, M. leprae, M. kasasii, M. avium,* Mycobacterium sp., *Legionella pneumophila, L. longbeachae, L. bozemanii,* Legionella sp., *Ricketsia rickettsii, Rickettsia typhi,* Rickettsia sp., *Ehrlichia chaffeensis, Ehrlichia phagocytophila* geno group, Ehrlichia sp., *Coxiella burnetii,* Leishmania sp, *Toxpolasma gondii, Trypanosoma cruzi, Chlamydia pneumoniae,* Chlamydia sp, *Listeria monocytogenes,* Listeria sp, and Histoplasma sp. In one embodiment of the present invention a recombinant BCG expressing the 30 kDa major extracellular protein of *M. tuberculosis* is administered to mammals using intradermal inoculations. However, it is understood that the vaccines of the present invention may be administered using any approach that will result in the appropriate immune response including, but not limited to, subcutaneous, intramuscular, intranasal, intraperitoneal, oral, or inhalation. Following a suitable post inoculation period, the mammals were challenged with an infectious *M. tuberculosis* aerosol. Mammals receiving the vaccine of the present invention were remarkably disease free as compared to mammals receiving BCG alone, the major extracellular protein alone, or any combinations thereof Other objects and features and advantages of the present invention will be apparent to those skilled in the art from a consideration of the following detailed description of preferred exemplary embodiments thereof taken in conjunction with the Figures which will first be described briefly.

DETAILED DESCRIPTION OF THE INVENTION

The present invention is directed generally to vaccines and immunotherapeutics for treating and preventing infections in humans and animals caused by intracellular pathogens. Specifically, the present invention is directed at optimizing intracellular pathogen antigen presentation to enable the immunotherapeutic and/or vaccine recipient to generate the maximum immune response to important therapeutic and prophylactic proteins. The present inventors, through years of research and experimentation, have surprisingly discovered that successful therapy and prophylaxis of intracellular pathogen infections using extracellular proteins derived from the intracellular pathogen is a function of protein presentation to the host.

Antigen presentation encompasses a group of variables that determine how a recipient processes and responds to an antigen. These variables can include, but are not limited to, adjuvants, vaccine component concentration, carrier molecules, haptens, dose frequency and route of administration. The present inventors have demonstrated that identical antigens compounded differently will result in statistically significant response variations in genetically similar hosts. For example, two vaccine preparations of the 30 kDa extracellular protein of *M. tuberculosis* were compounded using the same protein and adjuvant concentrations. One group of guinea pigs was administered a vaccine containing only the 30 kDa protein and adjuvant; a second guinea pig group was administered the same vaccine as the first except that IL-12 was added to the second vaccine. When the mean immune responses of both groups were compared, the guinea pigs receiving the vaccine plus IL-12 demonstrated a statistically significant superior immune response.

The present invention describes the union of two technologies, one known for over eighty years, the other a product of the 1990's. Together, they represent an entirely new and surprisingly effective approach to presenting intracellular pathogens' extracellular proteins to recipients and inducing remarkably robust protective immune responses thereto. The present inventors have attempted over 100 different antigen presentation methods using the extracellular proteins of *mycobacterium tuberculosis* as an exemplary intracellular pathogen. However, in spite of the many successes realized by the present inventors, none had induced an immune response superior to that seen using the BCG vaccine alone.

Briefly stated, and intended solely as a general example, the present invention includes vaccines for intracellular pathogens using attenuated, or avirulent, recombinant intracellular pathogens (the "vaccinating agent") that express and secrete recombinant immunogenic antigens of the same, another species, or both (the "immunogen(s)"); the vaccinating agent and immunogen(s) are referred to collectively as the "vaccines" of the present invention. The vaccines are administered using one or more routes, including, but not limited to, subcutaneous, intramuscular, intranasal, intraperitoneal, intradermal, oral, or inhalation. The vaccinating agents of the present invention survive within the recipient expressing and secreting the immunogen(s) in situ (status).

Without wishing to be bound to this theory, the present inventors have proposed that the immunogenic antigens of opportunistic pathogens such as Legionella sp. can illicit protective immune responses with greater ease than similar immunogenic antigens of more traditional animal pathogens such as mycobacterium sp. Selective pressures may have afforded pathogens such as Mycobacterium sp., that co-evolved with their natural hosts, immune evading mechanisms that incidental, or opportunistic, pathogens lack. Consequently, significantly more powerful vaccinating agents and immunogens must be developed to elicit protective immune responses against pathogenic Mycobacteria than those required to elicit protective immunity against pathogens for which humans are not a primary host.

The present inventors have previously demonstrated the extracellular proteins from the opportunistic intracellular pathogen Legionella sp. affords animals significant immune protection when administered in purified form or in cocktails using either complete or incomplete Freund's adjuvant. (See U.S. Pat. No. 5,108,745, which is incorporated herein by reference.) However, attempts to obtain similar protective immune responses using *M. tuberculosis* extracellular proteins under similar conditions have not been as successful. Consequently, the present inventors have proposed that over-expression of extracellular non-fusion proteins may be an important aspect of antigen presentation and the development of protective immune responses. However, it is understood that while the over-expression of non-fusion immunogenic extracellular proteins may be one important factor in eliciting protective immunity, it is not believed to be the only immunostimulatory factors the vaccines of the present invention provide.

The present invention is ideally suited for preparing highly effective immunoprotective vaccines against a variety of intracellular pathogens including, but not limited to BCG strains over-expressing the major extracellular non-fusion proteins of *M. tuberculosis, M. bovis* or *M. leprae*. Each vaccine of the present invention can express at least one immunogen of various molecular weights specific for a given intracellular pathogen. For example, the present inventers have previously identified *M. tuberculosis* immunogens that can include, but are not limited to, the major extracellular proteins 12 kDa, 14 kDa, 16 kDa, 23 kDa, 23.5 kDa, 30 kDa, 32A kDa, 32B kDa, 45 kDa, 58 kDa, 71 kDa, 80 kDa, 110 kDa and respective analogs, homologs and subunits thereof including recombinant non-fusion proteins, fusion proteins and derivatives thereof. (See pending U.S. patent applications Ser. Nos. 08/156,358, 09/157,689, 09/175,598, 09/226,539, and 09/322,116, the entire contents of which are hereby incorporated by reference). It is apparent to those of ordinary skill in the art that the molecular weights used to identify the major extracellular proteins of Mycobacteria and other intracellular pathogens are only intended to be approximations. Those skilled in the art of recombinant technology and molecular biology will realize that it is possible to co-express (co-translate) these proteins with additional amino acids, polypeptides and proteins, as it its also possible to express these proteins in truncated forms. The resulting modified proteins are still considered to be within the scope of the present invention whether termed native, non-fusion proteins, fusion proteins, hybrid proteins or chimeric proteins. For the purposes of the present invention, fusion proteins are defined to include, but not limited to, the products of two or more coding sequences from different genes that have been cloned together and that, after translation, form a single polypeptide sequence.

Antigen expression, including extracellular proteins, is generally enhanced when genes encoding for recombinant non-fusion proteins are located on, and under the control of, one or more plasmids (extrachromosomal DNA) rather than integrated into the host genome. Moreover, protein expression driven by promoter sequences specific for a particular protein provide enhanced expression and improved protein folding and processing of non-fusion-protein antigens. Therefore, the present invention provides recombinant extracellular non-fusion proteins encoded on extrachromosomal DNA that are controlled by non-heat shock gene promoters or non-stress protein gene promoters, preferably protein-specific promoter sequences.

The present invention provides recombinant attenuated intracellular pathogen vaccinating agents such as rBCG that express their own endogenous extracellular proteins in addition to recombinant extracellular non-fusion proteins of closely related and/or other intracellular pathogens. However, it has been demonstrated through 80 years of studies that BCG's endogenous extracellular proteins alone do not provide complete protection in all recipients. Furthermore, as will be explained in greater detail below, the present inventors have also demonstrated that merely co-injecting *M. tuberculosis* extracellular proteins along with traditional BCG does not result in vaccines superior to BCG alone.

In one embodiment of the present invention the vaccine includes a recombinant BCG vaccinating agent expressing only one immunogen, for example the 30 kDa major extracellular protein of *M. tuberculosis*. In another embodiment of the present invention the recombinant BCG may express two or more immunogens, for example the 23.5 kDa and the 30 kDa major extracellular proteins of *M. tuberculosis*. This latter embodiment may be particularly effective as a vaccine for preventing diseases in mammals. The present inventors have proposed the non-limiting theory that the simultaneous over expression of the 23.5 kDa and the 30 kDa major extracellular proteins of *M. tuberculosis* by a recombinant BCG may act synergistically to heighten the mammalian protective immune response against the intracellular pathogens of the present invention. This theory is partially based on the observation that wild-type and recombinant BCG are deletion mutants of *M. bovis* that do not naturally express their own 23.5 kDa major extracellular protein.

For brevity sake, and due to the immensely complex description that would ensue, but not intended as a limitation, the present invention will be more specifically described using a recombinant BCG as the vaccination agent and *M. tuberculosis* extracellular non-fusion proteins, specifically the 30 kDa major extracellular non-fusion protein, as an exemplary embodiment of the present invention. It is understood that any recombinant immunogenic antigen may be expressed by any recombinant attenuated intracellular pathogen, and that the vaccines of the present invention are not limited to BCG as the vaccinating agent and the major extracellular non-fusion proteins of *M. tuberculosis* as the immunogens.

In order to determine the effects of vaccinating agent strain variation, two different BCG strains were used to prepare the various embodiments of the present invention: BCG Tice and BCG Connaught. Wild-type *M. bovis* BCG Tice was purchased from Organon and wild-type *M. bovis* BCG Connaught was obtained from Connaught Laboratories, Toronto, Canada. The strains were maintained in 7H9 medium pH 6.7 (Difco) at 37° C. in a 5% $CO_2$-95% air atmosphere as unshaken cultures. Cultures were sonicated once or twice weekly for 5 min in a sonicating water bath to reduce bacterial clumping.

Recombinant BCG TICE (rBCG30 Tice) expressing the *M. tuberculosis* 30 kDa major extracellular non-fusion protein was prepared as follows. The plasmid pMTB30, a recombinant construct of the *E. coli*/mycobacteria shuttle plasmid pSMT3, was prepared as previously described by the present inventors in Harth, G., B.-Y. Lee and M. A. Horwitz. 1997. *High-level heterologous expression and secretion in rapidly growing nonpathogenic mycobacteria of four major Mycobacterium tuberculosis extracellular proteins considered to be leading vaccine candidates and drug targets.* Infect. Immun. 65:2321–2328, the entire contents of which are hereby incorporated by reference.

Briefly, plasmid pMTB30 was engineered to express the *M. tuberculosis* Erdman 30 kDa major extracellular non-fusion protein from its own promoter (or any non-heat shock and non-stress protein gene promoter) by inserting a large genomic DNA restriction fragment containing the 30 kDa non-fusion protein gene plus extensive flanking DNA sequences into the plasmid's multi-cloning site using methods known to those skilled in the art of recombinant DNA technology. The plasmid was first introduced into *E. coli* DH5α to obtain large quantities of the recombinant plasmid. The recombinant *E. coli* strain, which was unable to express the *M. tuberculosis* 30 kDa non-fusion protein, was grown in the presence of 250 μg/ml hygromycin and the plasmid insert's DNA sequence was determined in its entirety. The plasmid was introduced into *M. smegmatis* by electroporation using 6.25 kV/cm, 25 μF, and 1000 mΩ as the conditions yielding the largest number of positive transformants. The present inventors verified the presence of the recombinant plasmid by growth in the presence of 50 μg/ml hygromycin and the constitutive expression and export of recombinant 30 kDa non-fusion protein by polyacrylamide gel electrophoresis and immuoblotting with polyvalent, highly specific rabbit anti-30 kDa non-fusion protein immunoglobulin using methods known to those skilled in the art of recombinant DNA technology. Additionally, the inventors verified the correct expression and processing of the recombinant *M. tuberculosis* 30 kDa non-fusion protein, which was indistinguishable from its native counterpart by N-terminal amino acid sequencing.

The recombinant pSMT3 plasmid pMTB30 was subsequently introduced into *M. bovis* BCG Tice using 6.25 kV/cm, 25 μF, and 200 mΩ as the optimal electroporation conditions. Transformants were incubated in 7H9 medium supplemented with 2% glucose for 4 h at 37° C. in an environmental shaker and subsequently plated on 7H11 agar with 20 μg/ml hygromycin. The concentration of hygromycin was gradually increased to 50 μg/ml as the transformants were subcultured to a new growth medium. Recombinant BCG Tice cultures were maintained under the same conditions as the wild-type except that the 7H9 medium contained 50 μg/ml hygromycin.

Figure 1:
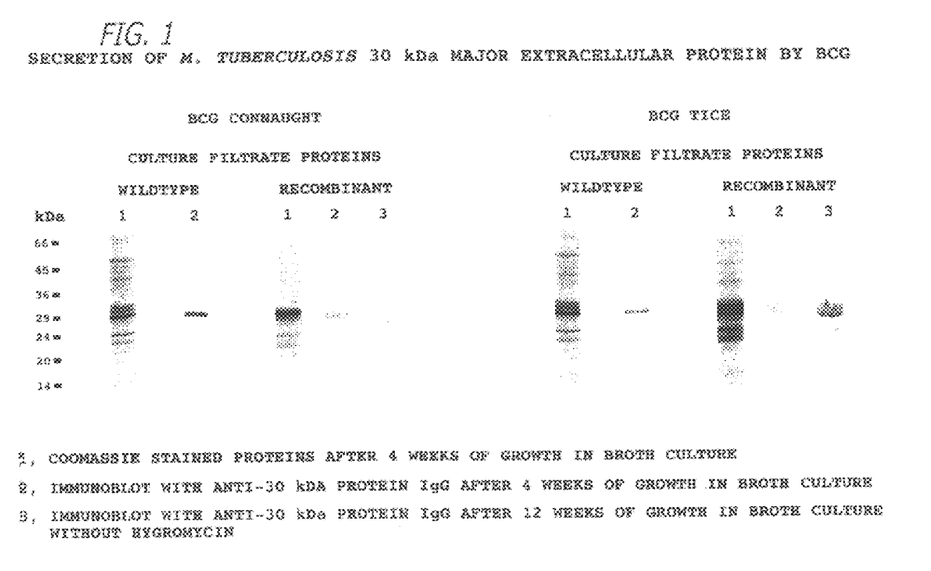
FIG. 1 depicts Coomassie blue stained gels labeled 1 illustrating the secretion of *Mycobacterium tuberculosis* recombinant 30 kDa by transformed strains of BCG from culture filtrates.
Figure 2:
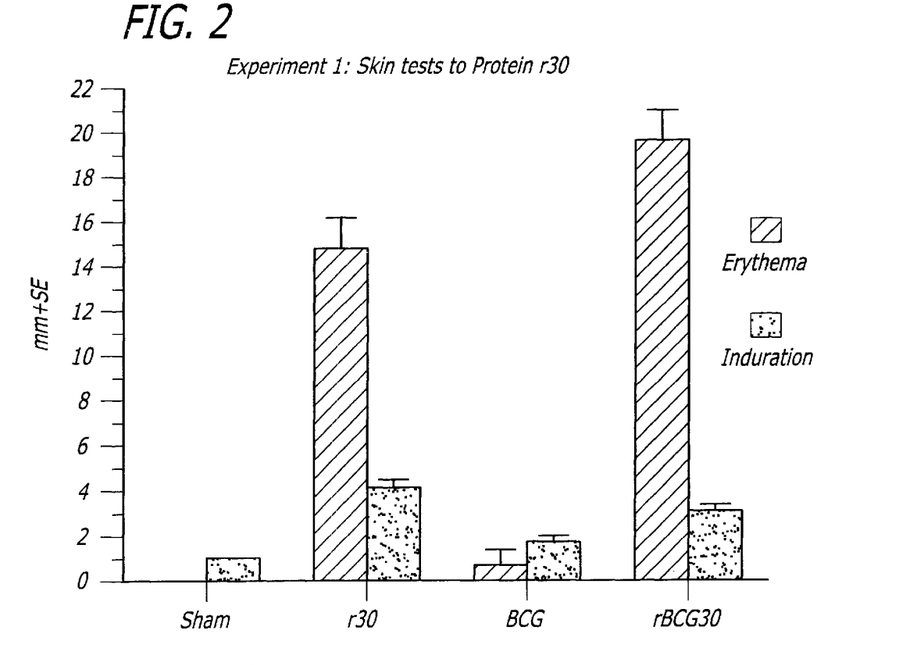
FIG. 2 graphically depicts the results from two experiments labeled 2 and 2*b* designed to compare skin tests results of guinea pigs inoculated with the recombinant BCG vaccine expressing the 30 kDa major extracellular protein of *M. tuberculosis,* with BCG alone, with the recombinant 30 kDa protein alone, or with a sham vaccine.
Figure 2B:
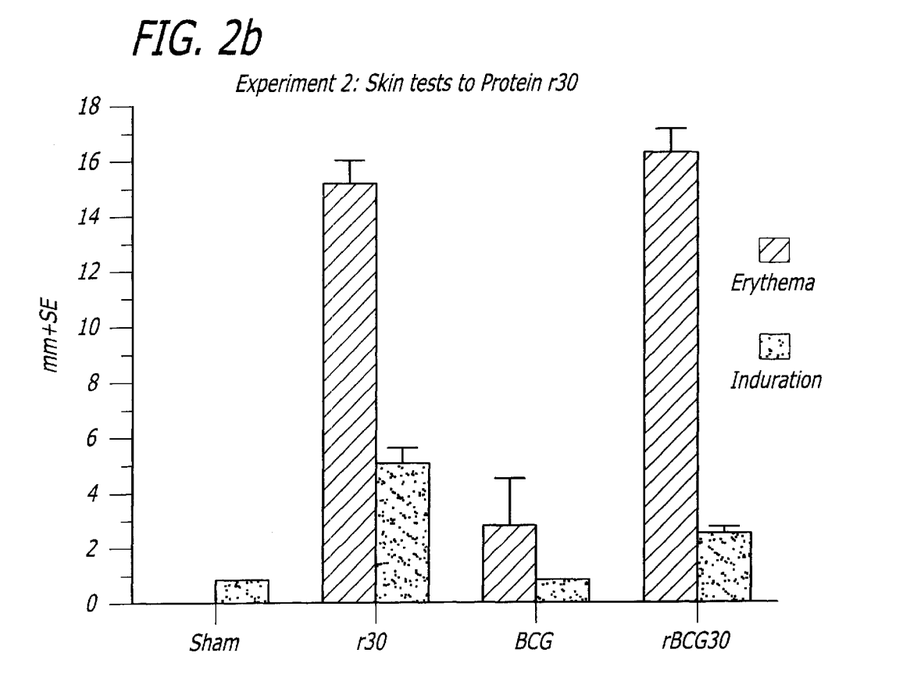
Figure 3:
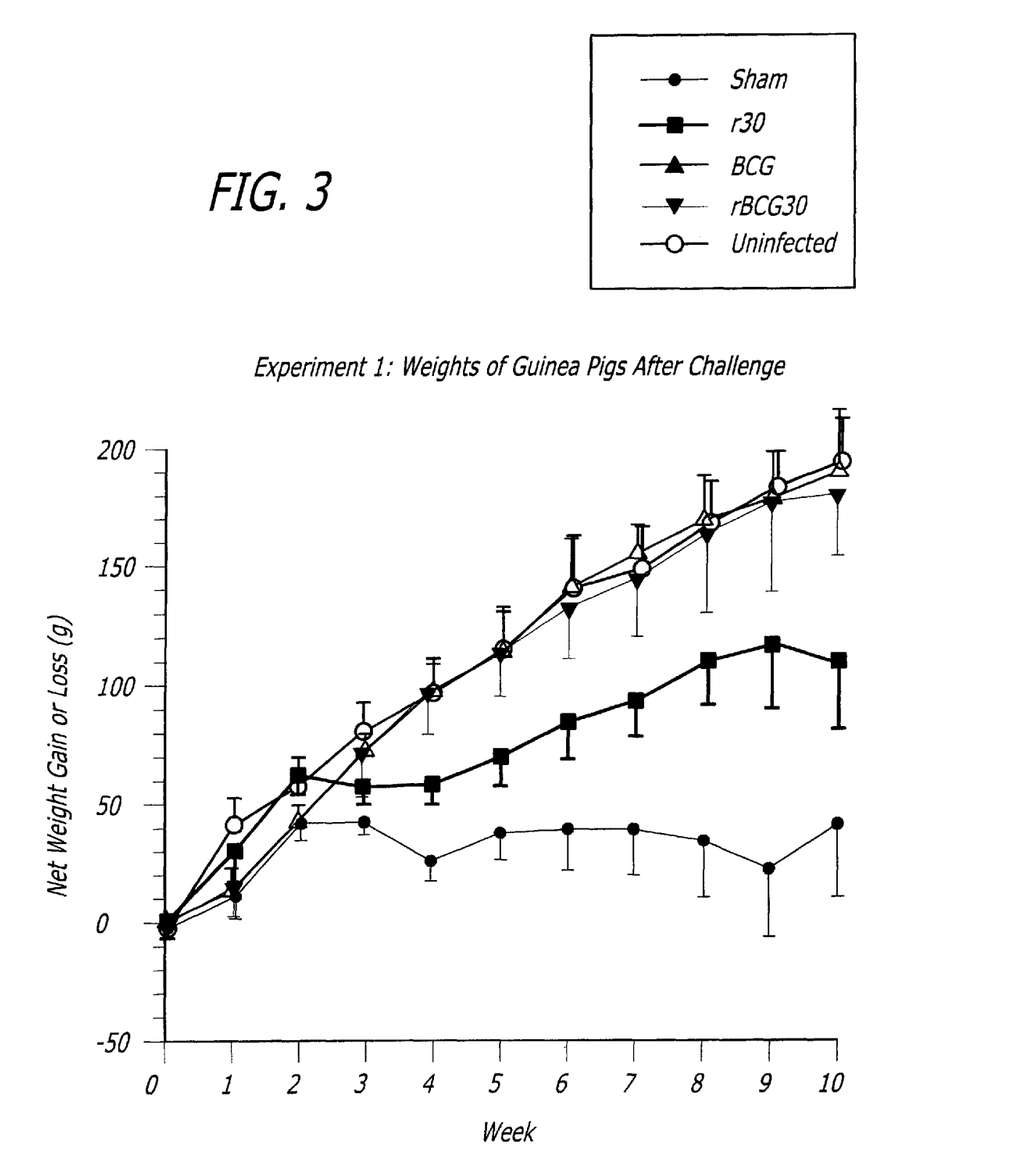
FIG. 3 graphically depicts the weight change in guinea pigs labeled 3 and 3*b* following post immunization challenge with *M. tuberculosis.*
Figure 3B:
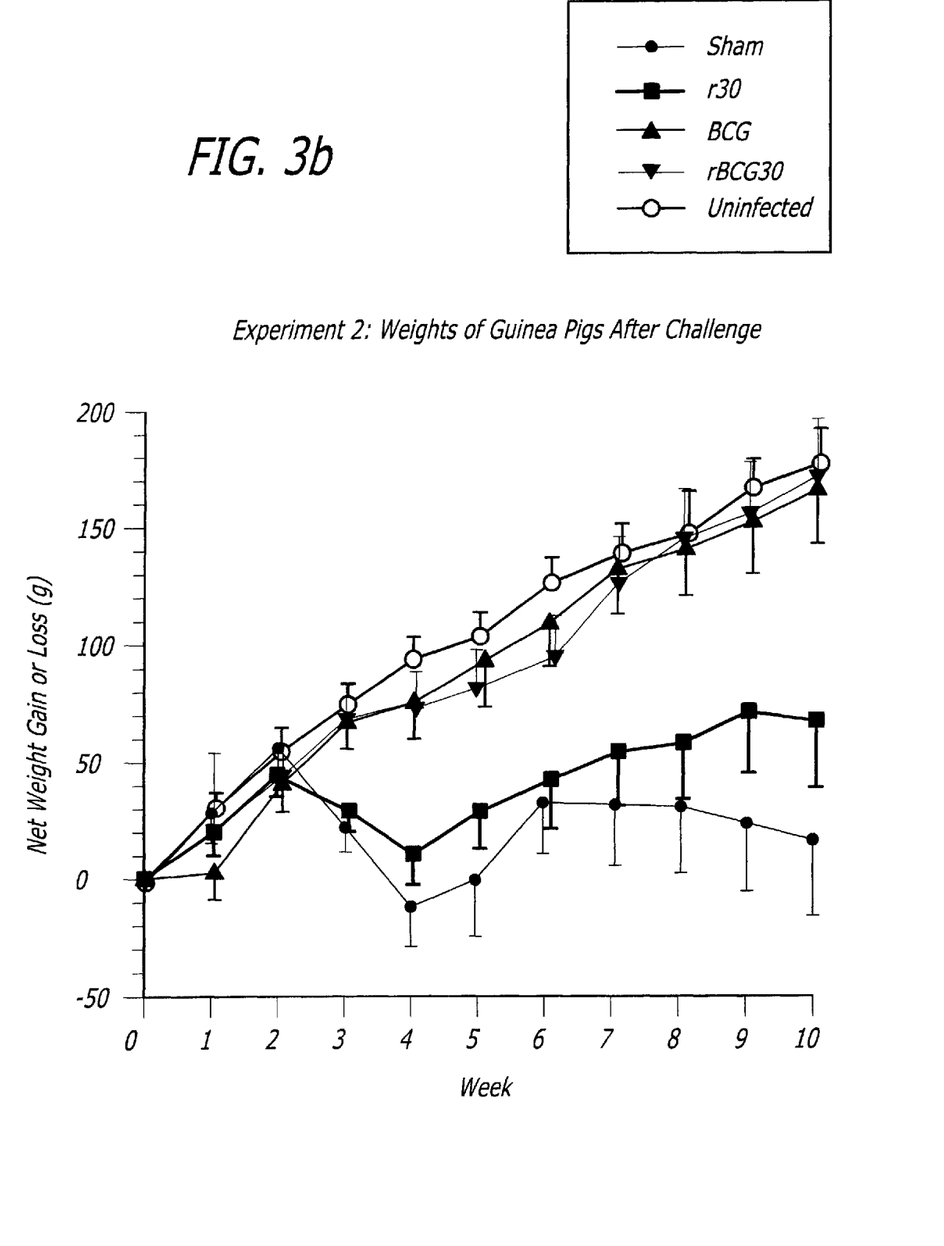
Figure 4:
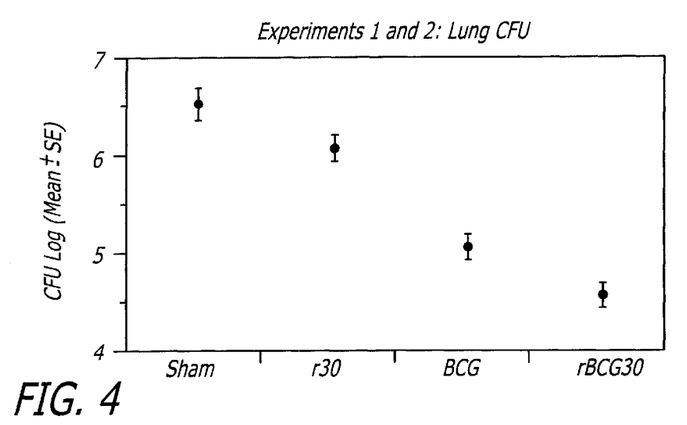
FIG. 4 graphically depicts Colony Forming Units (CFU) of infectious *M. tuberculosis* recovered from guinea pigs' lungs following post immunization challenge with *M. tuberculosis.*
Figure 4B:
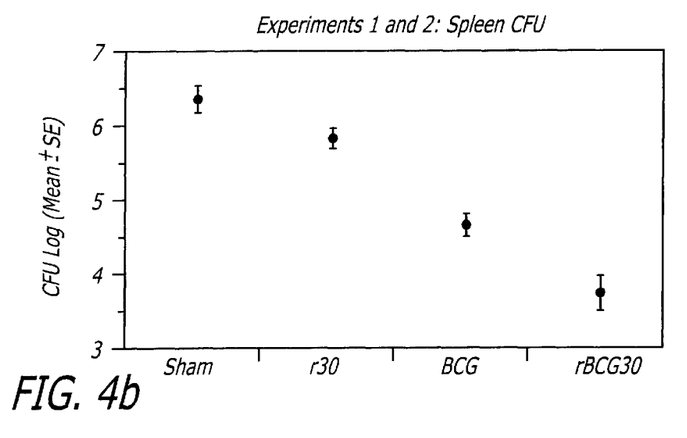
FIG. 4*b* graphically depicts Colony Forming Units (CFU) of infectious *M. tuberculosis* recovered from guinea pigs' spleens following post immunization challenge with *M. tuberculosis.*

The expression and export of recombinant *M. tuberculosis* 30 kDa non-fusion protein were verified by polyacrylamide gel electrophoresis and immunoblotting with polyvalent, highly specific rabbit anti-30 kDa non-fusion protein immunoglobulin. Typically, 1 in 10 transformants expressed and exported significantly larger quantities of recombinant non-fusion protein than the other transformants; 2 such transformants were chosen and a large stock of these transformants was prepared and frozen at −70° C. in 7H9 medium containing 10% glycerol. These transformants were used for vaccine efficacy studies in guinea pigs. FIG. 1*a* shows the expression of the *M. tuberculosis* 30 kDa major extracellular non-fusion protein by recombinant BCG Tice on SDS-PAGE gels and immunoblots. The recombinant strain expressed much more of the *M. tuberculosis* 30 kDa major extracellular non-fusion protein than the wild-type both on Coomassie blue stained gels and immunoblots.

Next a recombinant *M. bovis* BCG Connaught strain (rBCG30 Conn) expressing the *M. tuberculosis* 30 kDa major extracellular non-fusion protein was prepared similarly to that described above for recombinant BCG Tice (rBCG30 Tice) using the aforementioned pMTB30 plasmid. It was maintained in medium containing hygromycin at a concentration of 50 μg/ml under the same conditions as described for the recombinant BCG Tice strain. FIG. 1*b* shows the expression of the *M. tuberculosis* 30 kDa major extracellular non-fusion protein by recombinant BCG Connaught on SDS-PAGE gels and immunoblots. The recombinant strain expressed much more of the *M. tuberculosis* 30 kDa major extracellular non-fusion protein than the wild-type both on Coomassie blue stained gels and immunoblots.

Plasmid stability of recombinant strains of BCG was assessed biochemically. This biochemical analysis demonstrated that in the presence of hygromycin, broth cultures of the recombinant BCG strains maintain a steady level of recombinant non-fusion protein expression over a 3 month growth period. In the absence of hygromycin, the same cultures show only a slight decrease of non-fusion protein expression (on a per cell basis), indicating that the recombinant plasmid is stably maintained and only very gradually lost in bacteria growing without selective pressure (FIG. 1*a* and FIG. 1*b*, lane 3).

It is understood that using the methods described above in conjunction with methods known to those skilled in the art of recombinant DNA technology, recombinant BCG strains expressing the *M. tuberculosis* 32(A) kDa major extracellular non-fusion protein, 16 kDa major extracellular non-fusion protein, 23.5 kDa major extracellular non-fusion protein, and other *M. tuberculosis* major extracellular non-fusion proteins can be prepared. Furthermore, similar methodologies can be used to prepare recombinant BCG strains expressing *M. leprae* major extracellular non-fusion proteins including, but not limited to the *M. leprae* 30 kDa major extracellular non-fusion protein homolog of the *M. tuberculosis* 30 kDa major extracellular non-fusion protein (a.k.a. Antigen 85B), the *M. leprae* 32(A) kDa major extracellular non-fusion protein homolog of the *M. tuberculosis* 32(A) kDa major extracellular non-fusion protein (a.k.a. Antigen 85A), and other *M. leprae* major extracellular non-fusion proteins. Additionally, similar methodologies also can be used to prepare recombinant *M. bovis* BCG expressing the *M. bovis* 30 kDa major extracellular non-fusion protein homolog of the *M. tuberculosis* 30 kDa major extracellular non-fusion protein (a.k.a. Antigen 85B), the *M. bovis* 32(A) kDa major extracellular non-fusion protein homolog of the *M. tuberculosis* 32(A) kDa major extracellular protein (a.k.a. Antigen 85A), and other *M. bovis* major extracellular proteins.

Following the successful vaccine production the vaccines of the present invention are tested for safety and efficacy using an animal model. The studies utilized guinea pigs because the guinea pig model is especially relevant to human tuberculosis clinically, immunologically, and pathologically. In contrast to the mouse and rat, but like the human, the guinea pig a) is susceptible to low doses of aerosolized *M. tuberculosis*; b) exhibits strong cutaneous DTH to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of vaccine efficacy.

The immunization inoculums made in accordance with the teachings of the present invention were prepared from aliquots removed from logarithmically growing wild type or recombinant BCG cultures (the "bacteria"). Each aliquot of bacteria was pelleted by centrifugation at 3,500×g for 15 min and then washed with 1×phosphate buffered saline (1×PBS, 50 mM sodium phosphate pH 7, 150 mM sodium chloride). The immunization inoculums were then resuspended to a final concentration of $1\times10^4$ colony forming units per ml in 1×PBS and contained 1,000 viable bacteria per 100 μl.

Specific-pathogen free 250–300 g outbred male Hartley strain guinea pigs from Charles River Breeding Laboratories, in groups of 9, were immunized intradermally with one of the following: 1) BCG Connaught [$10^3$ Colony Forming Units (CFU)] one time only (time 0 weeks); 2) rBCG30 Connaught ($10^3$ CFU) one time only (time 0 weeks); 3) purified recombinant *M. tuberculosis* 30 kDa major extracellular non-fusion protein (r30), 100 μg in 100 μl Syntex adjuvant formulation (SAF), three times three weeks apart (time 0, 3, and 6 weeks); SAF consisted of Pluronic L121, squalane, and Tween 80, and in the first immunization, alanyl muramyl dipeptide; and 4) SAF only (100 μl) (Sham-immunized), three times three weeks apart (time 0, 3, and 6 weeks). An additional group of 3 animals was sham-immunized with SAF only (100 μl) and used as a skin test control. These and three to six other sham-immunized animals served as uninfected controls in the challenge experiments.

Nine weeks after the only immunization (BCG and rBCG30 groups) or first immunization (r30 group and sham-immunized skin-test group), guinea pigs were shaved over the back and injected intradermally with 10 μg of purified recombinant *M. tuberculosis* 30 kDa major extracellular non-fusion protein (r30) in 100 μl phosphate buffered saline. After 24 hours, the diameter of erythema and induration was measured. (A separate group of sham-immunized animals from the ones used in the challenge studies was used for skin-testing. Sham-immunized animals used in challenge studies were not skin-tested to eliminate the possibility that the skin-test itself might influence the outcome).

Nine weeks after the first or only immunization and immediately after skin-testing, animals were challenged with an aerosol generated from a 10 ml single-cell suspension containing $1\times10^5$ colony-forming units (CFU) of *M. tuberculosis. Mycobacterium tuberculosis* Erdman strain (ATCC 35801) was passaged through outbred guinea pi to maintain virulence, cultured on 7H11 agar, subjected to gentle sonication to obtain a single cell suspension, and frozen at −70° C. for use in animal challenge experiments. The challenge aerosol dose delivered ~40 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal were removed and cultured for CFU of *M. tuberculosis.*

In each of the two experiments, the sham-immunized animals and animals immunized with wild-type BCG exhibited little or no erythema and induration upon testing with recombinant 30 kDa *M. tuberculosis* major extracellular non-fusion protein (r30). In contrast, animals immunized with r30 or rBCG30 exhibited marked erythema and induration that was significantly higher than in the sham-immunized or wild-type BCG immunized animals (Table 1 and FIG. 2).

In each of the two experiments, uninfected controls gained weight normally after challenge as did animals immunized with either rBCG30 or wild-type BCG (FIG. 3). Indeed there were no significant differences in weight gain among these three groups. In contrast, sham-immunized animals and to a lesser extent r30 immunized animals, exhibited diminished weight gain over the course of the experiment (Table 2 and FIG. 3). Hence, after challenge with *M. tuberculosis,* both BCG and rBCG30 protected animals completely from weight loss, a major physical sign of tuberculosis in humans, and a hallmark of tuberculosis in the guinea pig model of this chronic infectious disease.

In each of the two experiments, at the end of the 10 week observation period, guinea pigs were euthanized and the right lung and spleen of each animal was removed aseptically and assayed for CFU of *M. tuberculosis.* Sham-immunized animals had the highest bacterial load in the lungs and spleen (Table 3 and FIG. 4*a* and FIG. 4*b*). Animals immunized with r30 had fewer organisms in the lungs and spleen than the sham-immunized animals; BCG-immunized animals had fewer organisms than r30-immunized animals; and remarkably, rBCG30-immunized animals had fewer organisms than BCG-immunized animals. Statistical tests employing two way factorial analysis of variance methods to compare means demonstrated that the means of the four "treatment" groups (Sham, r30, BCG, and rBCG30) in Experiment 1 were not significantly different from the means of the four treatment groups in Experiment 2 and that it was therefore appropriate to combine the data in the two experiments. The combined data is shown in Table 4 and FIG. 3. Of greatest interest and importance, the rBCG30-immunized animals had 0.5 log fewer organisms in the lungs and nearly 1 log fewer organisms in the spleen than BCG-immunized animals. On statistical analysis, employing analysis of variance methods to compare means and the Tukey-Fisher least significant difference (LSD) criterion to assess statistical significance, the mean of each of the four groups in both the lungs and spleens was significantly different from the mean of each of the others (Table 4). Differences between the rBCG30 and BCG immunized animals in the lungs were significant at $p=0.02$ and in the spleens at $p=0.001$. Paralleling the differences in CFU in the lungs, on gross inspection, lungs of rBCG30-immunized animals had less lung destruction than BCG-immunized animals (20±4% versus 35±5% mean±SE).

Thus, administration of recombinant BCG expressing the *M. tuberculosis* 30 kDa major extracellular non-fusion protein induced high level protection against aerosol challenge with *M. tuberculosis* in the highly susceptible guinea pig model of pulmonary tuberculosis. In contrast, as described in the examples below, administration of the same mycobacterial extracellular non-fusion protein (the *M. tuberculosis* recombinant 30 kDa major extracellular non-fusion protein) in adjuvant in combination with BCG does not induce high level protection against aerosol challenge with *M. tuberculosis;* nor does administration of recombinant *M. smegmatis* expressing the *M. tuberculosis* 30 kDa major extracellular non-fusion protein; nor does administration of the *M. tuberculosis* 30 kDa major extracellular non-fusion protein in microspheres that are of the same approximate size as BCG and like BCG slowly release the proteins over 60–90 days; nor does administration of the *M. tuberculosis* 30 kDa major extracellular non-fusion protein encapsulated in liposomes.

A very surprising aspect of this invention is that the rBCG30 strain induced protection superior to wild-type BCG even though the wild-type expresses and secretes an endogenous highly homologous 30 kDa major extracellular protein. (See FIG. 1). The gene encoding the 30 kDa protein from substrain BCG Connaught has not been sequenced. However, the sequence of the 30 kDa protein of two other substrains of BCG, deduced from the sequence of the cloned gene of these substrains, differs from the *M. tuberculosis* protein by only one amino acid (BCG Paris 1173 P2) or by 5 amino acids including two additional amino acids (BCG Tokyo). (See pages 3041–3042 of Harth, G., B.-Y. Lee, J. Wang, D. L. Clemens, and M. A. Horwitz. 1996. *Novel insights into the genetics, biochemistry, and immunocytochemistry of the 30-kilodalton major extracellular protein of Mycobacterium tuberculosis.* Infect. Immun. 64:3038–3047 the entire contents of which are herein incorporated by reference). Hence, the improved protection of the recombinant strain is unlikely to be due to the small amino acid difference between the recombinant and endogenous proteins. More likely, it is due to the enhanced expression of the recombinant non-fusion protein compared with the endogenous protein. If so, then the abundant expression obtained by using a high copy number plasmid was likely an important factor in the success of the recombinant vaccine.

TABLE 1

Cutaneous Delayed Type Hypersensitivity to the
*M. tuberculosis* 30 kDa Major Extracellular Protein

|  | Erythema (Mean Diameter ± SE) (mm) | Induration (Mean Diameter ± SE) (mm) |
|---|---|---|
| Experiment 1 | | |
| Sham-immunized | 0.0 ± 0.0 | 1.0 ± 0.0 |
| r30 | 15.0 ± 1.2 | 4.2 ± 0.3 |
| BCG | 0.8 ± 0.8 | 1.7 ± 0.2 |
| rBCG30 | 19.8 ± 2.2 | 3.1 ± 0.2 |
| Experiment 2 | | |
| Sham-immunized | 0.0 ± 0.0 | 1.0 ± 0.0 |
| r30 | 15.3 ± 0.9 | 5.2 ± 0.7 |
| BCG | 3.0 ± 1.5 | 1.0 ± 0.0 |
| rBCG30 | 16.5 ± 0.9 | 2.7 ± 0.4 |

TABLE 2

Net Weight Gain After Aerosol Challenge
with Virulent *M. tuberculosis* Erdman Strain

|  | Week 0 (Mean Weight ± SE) (g) | Week 10 (Mean Weight ± SE) (g) | Net Weight Gain (g) Week 0–10 (Mean ± SE) |
|---|---|---|---|
| Experiment 1 | | | |
| Sham-immunized | 763.1 ± 17.1 | 805.4 ± 27.8 | 42.3 ± 28.2 |
| r30 | 793.8 ± 21.6 | 906.3 ± 44.6 | 112.6 ± 32.0 |
| BCG | 763.8 ± 28.7 | 956.3 ± 45.4 | 192.5 ± 23.7 |
| rBCG30 | 767.8 ± 17.6 | 947.7 ± 31.3 | 179.9 ± 25.1 |
| Experiment 2 | | | |
| Sham-immunized | 839.1 ± 21.7 | 857.6 ± 32.4 | 18.5 ± 30.9 |
| r30 | 801.9 ± 36.3 | 888.6 ± 39.7 | 86.7 ± 28.3 |
| BCG | 796.6 ± 29.8 | 963.6 ± 19.8 | 167.0 ± 23.3 |
| rBCG30 | 785.7 ± 17.7 | 958.7 ± 27.7 | 173.0 ± 24.9 |

TABLE 3

Colony Forming Units (CFU) of *M. tuberculosis* in Lungs and Spleens
of Animals Challenged by Aerosol with *M. tuberculosis* Erdman Strain
Combined Experiments 1 and 2

|  | n | Lung CFU $Log_{10}$ (Mean ± SE) | Spleen CFU $Log_{10}$ (Mean ± SE) |
|---|---|---|---|
| Sham-immunized | 18 | 6.47 ± 0.17 | 6.27 ± 0.19 |
| r30 | 18 | 6.02 ± 0.14 | 5.73 ± 0.14 |
| BCG | 17 | 5.00 ± 0.13 | 4.57 ± 0.17 |
| rBCG30 | 18 | 4.53 ± 0.14 | 3.65 ± 0.25 |

TABLE 4

Summary of Statistical Analysis (ANOVA)
CFU in Lungs and Spleen
Combined Experiments 1 and 2

Lung

| Sham vs. r30 | p = 0.03 |
|---|---|
| r30 vs. BCG | p = 0.0001 |
| BCG vs. rBCG30 | p = 0.02 |

Spleen

| Sham vs. r30 | p = 0.05 |
|---|---|
| r30 vs. BCG | p = 0.0001 |
| BCG vs. rBCG30 | p = 0.001 |

TABLE 5

Colony Forming Units (CFU) of M. tuberculosis in Lungs and Spleens of Animals Challenged by Aerosol with M. tuberculosis Erdman Strain: Animals Immunized with BCG or with BCG plus Recombinant M. tuberculosis 30 kDa Protein in Adjuvant or Sham-immunized

|  | n | Lung CFU $\text{Log}_{10}$ (Mean ± SE) | Spleen CFU $\text{Log}_{10}$ (Mean ± SE) |
| --- | --- | --- | --- |
| Sham-immunized | 17 | 6.40 ± 0.18 | 5.65 ± 0.20 |
| BCG | 8 | 4.70 ± 0.13 | 2.91 ± 0.35 |
| BCG ± r30 | 9 | 5.30 ± 0.23 | 3.34 ± 0.37 |

TABLE 6

Colony Forming Units (CFU) of M. tuberculosis in Lungs and Spleens of Animals Challenged by Aerosol with M. tuberculosis Erdman Strain: Animals Immunized with Live Recombinant M. smegmatis Expressing the M. tuberculosis 30 kDa Major Extracellular Protein (rM. smegmatis30)

|  | n | Lung CFU $\text{Log}_{10}$ (Mean ± SE) | Spleen CFU $\text{Log}_{10}$ (Mean ± SE) |
| --- | --- | --- | --- |
| Sham-immunized | 9 | 6.63 ± 0.27 | 6.34 ± 0.29 |
| BCG | 8 | 4.61 ± 0.14 | 4.31 ± 0.27 |
| M. smegmatis Control | 9 | 5.92 ± 0.31 | 5.29 ± 0.34 |
| rM. smegmatis30 | 9 | 5.48 ± 0.26 | 5.55 ± 0.28 |

TABLE 7

Colony Forming Units (CFU) of M. tuberculosis in Lungs and Spleens of Animals Challenged by Aerosol with M. tuberculosis Erdman Strain: Animals Immunized with Microspheres That are of the Same Approximate Size as BCG and Like BCG Slowly Release the M. tuberculosis 30 kDa Major Extracellular Protein (r30) Animals Immunized with Liposomes That Contain the M. tuberculosis 30 kDa Major Extracellular Protein (r30)

|  | n | Lung CFU $\text{Log}_{10}$ (Mean ± SE) | Spleen CFU $\text{Log}_{10}$ (Mean ± SE) |
| --- | --- | --- | --- |
| Sham-immunized | 9 | 6.31 ± 0.19 | 6.20 ± 0.26 |
| BCG | 9 | 5.35 ± 0.14 | 4.81 ± 0.21 |
| rBCG30 | 9 | 4.48 ± 0.14 | 3.73 ± 0.33 |
| Control Microspheres | 9 | 6.67 ± 0.29 | 5.94 ± 0.32 |
| Microspheres with r30 (10 mg × 1) | 6 | 6.10 ± 0.32 | 5.93 ± 0.41 |
| Microspheres with r30 (3.3 mg × 3) | 9 | 6.42 ± 0.17 | 6.04 ± 0.28 |
| Control Liposomes | 9 | 6.24 ± 0.23 | 6.41 ± 0.21 |
| Liposomes with r30 | 9 | 5.77 ± 0.18 | 5.63 ± 0.16 |

The following Examples serve to illustrate the novel aspect of the present invention. Each example illustrates a means of delivering the immunogens of the present invention using techniques closely related to, but different from the vaccine of the present invention. Specifically, Example 1 demonstrates that when the immunogens of the present invention are administered with, but not expressed in vivo by BCG, a high level of protective immunity is not achieved.

Example 2 demonstrates that the in vivo expression of the immunogens of the present invention using a Mycobacterium sp. closely related to BCG, but unable to replicate in mammalian hosts, fails to induce significant levels of protection against challenge with M. tuberculosis. Examples 3 and 4 demonstrate that the slow release of the immunogens of the present invention by synthetic vaccine microcarriers also fails to induce significant levels of protection against challenge with M. tuberculosis.

Therefore, the following Examples serve to highlight the completely surprising and remarkable advance that the intracellular pathogen vaccines of the present invention represents to the field of infectious disease immunology.

EXAMPLES

Example 1

Figure 5:
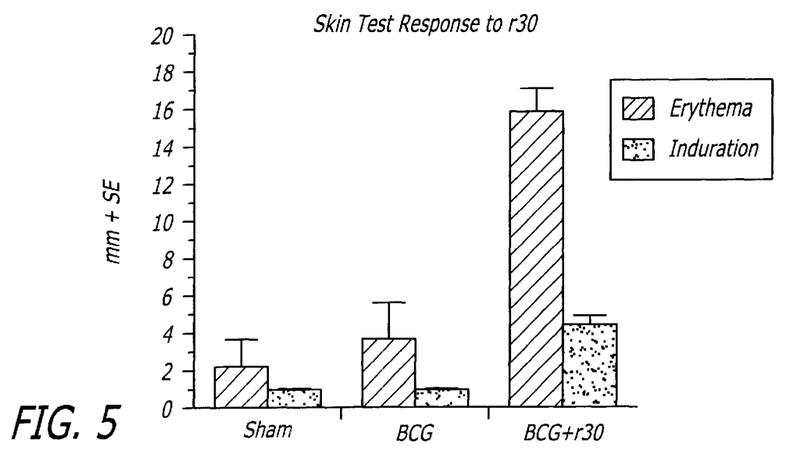
FIG. 5 graphically depicts the skin test response of guinea pigs to sham vaccine, BCG alone and BCG administered with recombinant 30 kDa of *M. tuberculosis.*

Immunization of Guinea Pigs with BCG Plus Recombinant M. tuberculosis 30 kDa Major Extracellular Protein (r30) does not Induce High Level Protection against Challenge with M. tuberculosis We previously immunized guinea pigs with BCG plus r30 in a powerful adjuvant (SAF, Syntex Adjuvant Formulation). The r30 protein (100 μg per immunization) was administered intradermally three times. This induced a strong cutaneous delayed-type hypersensitivity (C-DTH) response to r30 (FIG. 5). Indeed, the C-DTH response was comparable to that induced by recombinant BCG expressing r30. Nevertheless, immunization with both BCG and r30 did not induce high level protection against challenge with M. tuberculosis (Table 5). Animals immunized with both BCG and r30 did not have lower levels of CFU in the lungs and spleen than animals immunized with BCG alone. This result is in direct contrast to the result described above in which animals immunized with recombinant BCQ expressing r30 exhibited high level protection when challenged with M. tuberculosis.

Example 2

Immunization of Guinea Pigs with Live Recombinant M. smegmatis Expressing the M. tuberculosis 30 kDa Major Extracellular Protein (r30) in a Form Indistinguishable from the Native Form does not Induce High Level Protection against Challenge with M. tuberculosis In one of the same experiments in which we immunized animals with BCG, we immunized guinea pigs with live recombinant M. smegmatis expressing the M. tuberculosis 30 kDa major extracellular protein (r30) in a form indistinguishable from the native form. The expression and secretion of the M. tuberculosis 30 kDa major extracellular protein (r30) by M. smegmatis was equal to or greater than that of the recombinant BCG strain expressing and secreting the M. tuberculosis 30 kDa major extracellular protein. Moreover, the dose of recombinant M. smegmatis, $10^9$ bacteria, was very high, one million times the dose of recombinant BCG ($10^3$ bacteria), to more than compensate for the poor multiplication of M. smegmatis in the animal host. To compensate even further, the recombinant M. smegmatis was administered three times intradermally, whereas the recombinant BCG was administered only once intradermally. Immunization with recombinant M. smegmatis expressing the r30 protein induced a strong cutaneous delayed-type hypersensitivity (C-DTH) response to r30. Indeed, the C-DTH response was comparable to or greater than that induced by recombinant BCG expressing r30. Nevertheless, the live recombinant M. smegmatis expressing the M. tuberculosis 30 kDa major extracellular protein did not induce high level protection against challenge with M. tuberculosis (Table 6). Animals immunized with the live recombinant M. smegmatis expressing the M. tuberculosis 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with M. tuberculosis.

Example 3

Immunization of Guinea Pigs with Microspheres that are of the Same Approximate Size as BCG and Like BCG Slowly Release the *M. tuberculosis* 30 kDa Major Extracellular Protein (r30) over 60–90 Days does not Induce High Level Protection against Challenge with *M. tuberculosis*

In one of the same experiments in which we immunized animals with rBCG30 and BCG, we immunized guinea pigs with microspheres that are of the same approximate size as BCG and like BCG slowly release the *M. tuberculosis* 30 kDa major extracellular protein (r30) over 60–90 days. One set of animals was immunized once with microspheres containing 10 mg of r30. Another set of animals was immunized three times with microspheres containing 3.3 mg of r30. This amount was calculated to greatly exceed the amount of r30 protein expressed by the recombinant BCG strain. Immunization with either regimen of microspheres induced a strong cutaneous delayed-type hypersensitivity (C-DTH) response to r30. Indeed, the C-DTH response was comparable to that induced by recombinant BCG expressing r30. Nevertheless, immunization with the microspheres that are of the same approximate size as BCG and like BCG slowly release the *M. tuberculosis* 30 kDa major extracellular protein did not induce high level protection against challenge with *M. tuberculosis* (Table 7). Animals immunized with the microspheres did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

Example 4

Immunization of Guinea Pigs with Liposomes Containing the *M. tuberculosis* 30 kDa Major Extracellular Protein does not Induce High Level Protection against Challenge with *M. tuberculosis*

In the same experiment as in Example 3, we immunized guinea pigs with liposomes containing the *M. tuberculosis* 30 kDa major extracellular protein. The animals were immunized three times with liposomes containing 50 μg of r30. This induced a moderately strong cutaneous delayed-type hypersensitivity (C-DTH) response to r30. The C-DTH response was greater than that induced by BCG and control liposomes but less than that induced by recombinant BCG expressing r30. Nevertheless, immunization with liposomes containing the *M. tuberculosis* 30 kDa major extracellular protein did not induce high level protection against challenge with *M. tuberculosis* (Table 7). Animals immunized with the liposomes containing the *M. tuberculosis* 30 kDa major extracellular protein did not have lower levels of CFU in the lungs and spleen than animals immunized with BCG alone. This result is in direct contrast to the result described above in which animals immunized with recombinant BCG expressing r30 exhibited high level protection when challenged with *M. tuberculosis*.

The vaccines of the present invention represent an entirely new approach to the therapeutic and prophylactic treatment of intracellular pathogens. Through a series of well designed experiments and thoughtful analysis, the present inventors have thoroughly demonstrated that protective immunity is only achieved when a precisely selected intracellular pathogen, or closely related species, is transformed to express recombinant extracellular proteins of the same or different intracellular pathogen in accordance with the teachings of the present invention.

The present invention can also be used to provide prophylactic and therapeutic benefits against multiple intracellular pathogens simultaneously. For example a recombinant attenuated intracellular vaccinating agent like *M. bovis* can be designed to expressed immuno-protective immunogens against *M. tuberculosis* and Legionella sp. simultaneously. Consequently, great efficiencies in delivering vaccines could be accomplished. The non-limiting examples of recombinant BCG expressing the major extracellular proteins of *M. tuberculosis* not only serve as a fully enabling embodiment of the present invention, but represent a significant advance to medicine, and humanity as a whole.

Therefore, it is apparent that while a preferred embodiment of the invention has been shown and described, various modifications and changes may be made without departing from the true spirit and scope of the invention.

We claim:

1. An immunogenic composition comprising:

a recombinant Bacille Calmette-Guérin (BCG) having an extrachromosomal nucleic acid sequence comprising a gene encoding for a *Mycobacteria tuberculosis* 30 kDa major extracellular protein, wherein said *Mycobacteria tuberculosis* 30 kDa major extracellular protein is over expressed and secreted.

2. An immunogenic composition comprising:

a recombinant BCG having an extrachromosomal nucleic acid sequence comprising a gene encoding for a *Mycobacteria tuberculosis* 30 kDa major extracellular protein, wherein said *Mycobacteria tuberculosis* 30 kDa major extracellular protein is over expressed and secreted such that an immune response is induced in an animal.

3. The immunogenic composition according to claim 1 or 2 wherein said nucleic acid sequence is under the control of a promoter that is not a heat shock promoter or a stress protein promoter.

4. The immunogenic composition according to claim 1 or 2 wherein said major extracellular protein is a non-fusion protein.

5. An immunogenic composition comprising:

a recombinant BCG having an extrachromosomal nucleic acid sequence comprising a gene encoding for *Mycobacterium tuberculosis* 30 kDa major extracellular non-fusion protein under the control of a promoter wherein said promoter is not a heat shock promoter or stress protein promoter and wherein said 30 kDa major extracellular non-fusion protein is over expressed and secreted such that an immune response is induced in an animal.

6. An immunogenic composition comprising:

a recombinant BCG having an extrachromosomal nucleic acid comprising a gene encoding for *Mycobacterium tuberculosis* 30 kDa major extracellular non-fusion protein under the control of a promoter wherein said promoter is not a heat shock promoter or stress protein promoter and wherein said *Mycobacterium tuberculosis* 30 kDa major extracellular non-fusion protein is over expressed and secreted from said recombinant BCG such that both a humoral and a cellular immune response is induced in an animal.

\* \* \* \* \*